United States Patent [19]
Elbrecht et al.

[11] Patent Number: 6,162,218
[45] Date of Patent: Dec. 19, 2000

[54] METHOD AND ARRANGEMENT FOR PHOTOABLATION

[75] Inventors: Jens Elbrecht; Udo Holzapfel; Thomas Kloss, all of Jena; Eckhard Schroeder, Eckental; Bernhard Seitz, Wogau; Ingolf Streit, Rothenstein, all of Germany

[73] Assignee: Aesculap-Meditec GmbH, Jena, Germany

[21] Appl. No.: 09/039,597

[22] Filed: Mar. 16, 1998

[30] Foreign Application Priority Data

Mar. 16, 1997 [DE] Germany .............................. 197 10 676

[51] Int. Cl.⁷ ....................................................... A61B 8/00
[52] U.S. Cl. ................................................... 606/41; 606/9
[58] Field of Search ........................... 606/2, 7; 604/114; 600/632, 8

[56] References Cited

U.S. PATENT DOCUMENTS

| | | |
|---|---|---|
| 4,850,352 | 7/1989 | Johnson . |
| 5,181,916 | 1/1993 | Reynolds et al. . |
| 5,683,366 | 11/1997 | Egger et al. .............................. 604/114 |
| 5,871,469 | 2/1999 | Eggers et al. ............................ 604/114 |
| 5,941,873 | 8/1999 | Korenfeld . |

FOREIGN PATENT DOCUMENTS 0 538 641   4/1993   Germany .

Primary Examiner—Marvin M. Lateef
Assistant Examiner—Maulin Patel
Attorney, Agent, or Firm—Reed Smith LLP

[57] ABSTRACT

A method for photoablation in the field of dermatological medicine and to an arrangement for carrying out this method is disclosed in which the laser radiation and the outlet channel for the laser radiation are directed to a portion of skin to be treated during the treatment and the outlet opening is positioned near the treatment area. In this method, the area to be treated is subjected to a suction vacuum during treatment over its entire extent. In particular, the outlet opening communicates with a device for generating a vacuum.

37 Claims, 2 Drawing Sheets

METHOD AND ARRANGEMENT FOR PHOTOABLATION

BACKGROUND OF THE INVENTION a) Field of the Invention

The invention is directed to a method for photoablation in the field of dermatological medicine in which an area on a surface of the skin is swept over by a laser beam and thus subjected to treatment. It is further directed to an arrangement for photoablation in the field of dermatological medicine by means of laser radiation with optical component groups for protected guidance of the laser radiation, with closing or terminating optics at the point where the laser radiation passes into the open air, and with a tubular outlet channel by which the free laser radiation is surrounded proceeding from the terminating optics and which has an outlet opening for the laser radiation at its end portion opposite from the terminating optics, wherein, during treatment, the laser radiation and the outlet channel are directed toward an area to be treated on the surface of the skin and the outlet opening is positioned near the area.

b) Description of the Related Art

When a continuous laser beam strikes the skin for longer than 10 milliseconds, electromagnetic energy is converted into thermal energy which can be used to coagulate diseased tissue. If short laser pulses with a pulse duration in the range of nanoseconds and microseconds are used for treatment, mechanical-destructive tissue effects can be achieved without substantial thermal damage to the skin or to the biological matter in the target area.

It is known to use laser radiation for removal of material in this almost non-thermal process, also called photoablation. This possibility is already made use of all over the world, for example, to treat bone cartilage and hard tooth tissue, as well as in dermatological therapy. In dermatology, there is, above all, the possibility of treating various skin alterations from disfigured tissue to tumors.

At present, lasers are used in dermatology worldwide for the treatment of burns, for removal of tattoos and for skin renewal (resurfacing). This already indicates that such therapy is used predominantly for improving the quality of life of the patient and for cosmetic adjustment.

Medical-engineering instruments for carrying out the therapies mentioned above basically comprise a laser radiation source and a handpiece which serves to direct the laser radiation emitted by the laser radiation source to the target area of the part of the body to be treated. In order for the handpiece to be constructed with small dimensions and for the purpose of convenient handling with the least possible hindrance, the laser radiation source and handpiece are usually separated structurally and spatially, wherein a beam guiding unit is provided for transmitting the laser radiation from the radiation source to the handpiece. The beam guiding unit can comprise a plurality of rigid transmission members which are connected with one another in an articulated manner or as a flexible fiber-optic device. The handpiece has outlet optics and an outlet opening for the laser radiation which is to be directed to the target area.

DE 44 01 989 A1 describes a medical handpiece which serves to direct a laser beam emitted from a laser radiation source onto the part of the body to be treated. This handpiece comprises a housing and a laser radiation source integrated in the housing. By integrating the laser radiation source in the housing, the beam guiding unit can be omitted entirely, so that the handling of the medical handpiece is not impaired by mechanically restricted movement.

A recurring problem in ablation of biological matter by laser radiation and in the use of handpieces consists in that the particles removed from the treated surface impair the air quality in the immediate environment of the treatment location and also in the handpiece itself, e.g., in the outlet channel for the laser radiation. The particles settle on the outlet optics for the optical beam path in the handpiece in a disadvantageous manner and lead to unpleasant odor for the patient and the person carrying out the treatment because biological matter also evaporates during the treatment.

In order to prevent this, it is necessary to remove the detached particles and the resulting fumes from the place of origin or at least to prevent the particles from settling on the optics in the handpiece. For this reason and, finally, also for the purpose of protecting the medical personnel and the patient from the harmful and foul-smelling fumes, exhaust systems have been developed which, as separately engineered units, comprise a base device containing a suction source and a filter, and a tube-prefilter system. Accessories for devices of the kind mentioned above include suction tubes which must be positioned in the vicinity of the treated location so that ablation debris or ablation waste products can be intercepted. The disadvantages of this device consist on the one hand in that the suction tube arranged in the vicinity of the treatment location restricts the freedom of movement of the handpiece during the laser treatment and, on the other hand, when changing the treatment location it is necessary to readjust the handpiece or the target direction of the laser beam so that the suction device remains effectively directed to the treatment location.

In further conventional handpieces such as those described, e.g., in U.S. Pat. No. 5,344,418, flow channels for gases or air are provided inside the handpiece which end in the vicinity of the outlet opening for the laser beam and, from that location, direct a flow of gas or air to the location to be treated. This primarily provides for a cooling (although an uneven cooling) of the treated skin region, but also results in a secondary effect at least in that the ablation waste products are blown away from the handpiece and from the treated skin area. This also does not solve the problem of contaminated air and unpleasant odor. Moreover, the treated skin portion is not thermally affected in a uniform manner, since the gas flow or air flow must pass over the target area laterally, wherein the temperature of the gas or air changes and the cooling effect may not be the same as it was to start with by time it reaches the end of the target area.

In addition to the handpieces described thus far for ablation of biological matter, other handpieces are known which are outfitted with a spacer serving to adjust a definite distance between the beam outlet opening of the handpiece and the treatment location. The spacer is a roughly rod-shaped object which is fastened to the handpiece by one end portion in the vicinity of the outlet opening for the laser radiation, the opposite end portion being placed lightly on the skin in a location in the immediate vicinity of the treatment location during treatment. This ensures that the laser outlet opening and outlet optics for the laser beam are at an at least roughly constant distance from the treatment location and provides for proper focussing of the laser beam on the treatment location.

It is known to provide spacers of this kind with a suction port on the one hand and to connect the spacers with an exhaust device on the other hand, wherein the suction opening is oriented in such a way that ablation waste products such as particles and fumes are intercepted by the suction port and carried away to the exhaust device through the spacer. However, it is disadvantageous that these arrangements only operate effectively when the suction port in the spacer can be positioned in the immediate vicinity of the laser beam or treatment location and can also remain there. As soon as the distance between the laser beam and suction opening increases, as is the case, e.g., when treating larger skin surfaces by means of laser scanners, the effectiveness of this exhaust device decreases as the distance increases between the laser radiation and the suction port.

OBJECT AND SUMMARY OF THE INVENTION

The primary object of the invention is to provide a method for photoablation in the field of dermatological medicine in which an area on the surface of the skin is swept over by a laser beam and, in this way, subjected to treatment.

According to the invention, this object is met in that the area to be treated is subjected to a suction vacuum during treatment over its entire extent. Accordingly, in contrast to the method known in the prior art, the suction is carried out during treatment at the immediate location of the laser beam and acts on the skin, but, beyond this, the suction is effected in a permanent manner over the entire region swept over by the laser beam during a period of time. This is particularly advantageous when a scanned laser beam which scans an area on the surface of the skin chosen for treatment is used for photoablation. This treated area can extend over a surface area of several square millimeters, e.g., 10 mm×10 mm, while the laser beam has a diameter of only 2 to 3 mm. The laser beam scans the treatment area in time intervals, while the suction is carried out uniformly over the entire treated area for the full duration of the scanning.

It is provided in an advantageous configuration of the invention that the suction vacuum is effected through a mouth opening of a suction tube positioned over the target area. For this purpose, the cross section of the suction tube or mouth opening arranged over the treatment area should essentially correspond to the surface area of the treatment area. In a very advantageous configuration, the cross section of the suction tube can be slightly larger than the surface area of the treated surface area. Further advantageous configurations are provided in that the cross section of the suction tube arranged over the treated area is 5% to 10% greater than the treated area. In a very advantageous manner, by means of the invention, the mouth opening of the suction tube can also be used as an outlet opening for the laser beam, and vice versa.

Further, the edge of the mouth opening of the suction tube should be positioned at a distance from the treated area of 10 mm to 80 mm, especially 15 mm to 60 mm, preferably 20 mm to 50 mm, and most preferably 30 mm to 35 mm. The suction vacuum should be selected in such a way that the maximum flow velocity in the mouth opening of the suction tube is 650 liters per minute. In a particularly advantageous manner, the suction vacuum can be selected in such a way that the mean flow velocity in the mouth opening of the suction tube is approximately 400 liters per minute.

In this way, it is advantageously ensured that the sucked in air flows from all sides, so-to-speak in a star-shaped manner, over the surface of the skin onto the area to be treated and, from there, at a right angle to the surface of the skin, i.e., essentially in the direction opposite to the radiation direction of the laser, to the mouth opening of the suction tube and is carried away inside the suction tube. In so doing, all particles as well as the fumes occurring during the ablation procedure are advantageously intercepted by the air flow and carried away. In this way, ablation waste products are prevented from spreading into the surrounding air and disturbing the treatment personnel and patient. The ablation waste products are also prevented from settling on parts of the optical or medical equipment essential to operation and impairing operability. A further substantial advantage consists in that the air flowing past the skin and past the area to be treated has a positive effect on treatment. This positive influence arises essentially from the cooling and temperature-correcting effect which is brought about by the flowing air, which effect is more uniform than in the prior art and is also perceived by the patient as a pleasant sensation (which is an advantageous secondary effect). A further positive influence on the treatment at the location of the treated area results in that the air undergoes a change in flow direction immediately above the treatment area. This results in a central flow channel in the center of the treated area, the direction of flow of this central flow channel being oriented opposite to the laser radiation direction, while the impinging air flow moves toward this center proceeding from all sides in a star-shaped manner.

A further object of the invention consists in further developing an arrangement for photoablation in such a way that ablation waste products such as particles and fumes are removed from the treated area such that a soiling of the outlet optics for the laser beam and disturbance of the personnel and patients are prevented even more effectively.

In accordance with the invention, this object is met in that the outlet opening communicates with a device for generating a vacuum. For this purpose, an air extraction device or exhaust device should be provided as the device for generating a vacuum. A development of the invention provides that the wall of the tubular outlet channel has at least one through-opening extending from its inner region to the outside and that the outside is connected to the exhaust device. The outlet opening for the laser beam can advantageously take over the function of the mouth opening of the suction tube, and vice versa.

In further very advantageous configurations of the invention, a plurality of through-openings are provided in the wall of the outlet channel, wherein these through-openings are distributed in a radially symmetric manner along a circumference extending around the center axis of the laser beam or, alternatively, the through-openings can be distributed along the circumference extending around the center axis of the laser beam so as to be spaced at different intervals from one another. An advantage in this arrangement is that the particles and fumes occurring as by-products of the photoablation procedure are effectively extracted from the treated skin portion. Due to the fact that the extracted air flow is sucked through the entire outlet opening into the inner region of the outlet channel, the particles or fumes are prevented from being removed laterally from the treated location and entering the surrounding air. The particles and gas fumes sucked through the outlet opening into the inner region of the outlet channel are conveyed by the air flow through the through-openings provided in the sides of the outlet channel toward the outside of the outlet channel and from the latter to the exhaust device. This not only prevents these ablation waste products from contaminating the air, but also prevents them from settling on the terminating optics for the laser beam. Therefore, the terminating optics are successfully protected from soiling (the terminating optics can be constructed as plano-windows or as beam-shaping elements). A further substantial advantage results in that the particles and gases are removed very quickly from the laser radiation area so that an uneven distribution of energy within the laser beam brought about by particles or fumes crossing the laser beam is prevented from the outset.

This ensures a reliable operation of the arrangement and a high efficiency in dermatological medical treatment. The fact that a temperature-correcting air flow or air whirling is generated over the portion of skin to be treated also contributes to the success of the treatment and accordingly to increased effectiveness.

In a very advantageous configuration of the invention, the circumference along which the through-openings are arranged around the center axis of the laser beam is provided near the outlet opening of the outlet channel. This ensures that the ablation waste products to be extracted do not penetrate into the outlet channel even as far as the outlet optics, but rather are carried off at the very start of the outlet channel laterally through its wall.

The through-openings in the wall of the outlet channel can have different or identical geometric shapes, e.g., they are advantageously shaped as circular holes. Alternatively, however, it can also be advantageous under certain conditions to form the through-openings as slots, wherein the longer side edge of each slot should be oriented parallel to the center axis of the laser beam. It is also possible to form the through-openings as trapezoidal slots, wherein the smaller slot width should be oriented toward the outlet opening.

All of these variants ensure an effective removal of particles and fumes and accordingly guarantee the cleanliness of the surroundings of the treatment location and of the terminating optics. Effective removal of particles and fumes is assisted, for example, through a configuration of the outlet channel in which the sum of the surfaces of the through-openings is roughly equal to the cross-sectional area of the following suction line. In this way optimum flow conditions are provided from the through-openings to the exhaust device. It is further possible to provide a construction of the handpiece in which a throttle device is provided for the cross section of the through-openings or of the following suction line. This provides for the possibility of influencing the throughput and flow velocity of the exhaust air proceeding from the handpiece.

In further configurations, all through-openings can be arranged at the same distance from the outlet opening considered in the longitudinal direction of the terminating optics, or the through-openings can be arranged on a plurality of circumferences extending around the center axis of the laser beam and these individual circumferences can be provided at different distances from the outlet opening considered in the longitudinal direction of the terminating optics.

In a very advantageous configuration of the invention, the outlet channel is constructed as a double tube, wherein the core region of the double tube is identical to the inner region of the outlet channel, the inner surface of the double tube is identical to the wall of the outlet channel, the through-openings lead from the core region into the intermediate region between the inner surface of the double tube and the outer surface of the double tube, and the intermediate region is connected with the exhaust device. In addition, the outer surface of the double tube can be constructed as a handle. This construction makes it possible for the treating physician to grasp the outlet channel by its outer surface and to direct the laser radiation easily onto the treatment area by hand. In so doing, the air flow, including the removed particles, is guided between the inner region and the handle and flows to the exhaust device.

In a further very advantageous construction, the outlet channel is connected with the rest of the component parts of the arrangement so as to be hermetically sealed by its end portion located at the terminating optics, but so as to be detachable. In this way the outlet channel can be removed from the rest of the component groups of the arrangement and cleaned at any time and the terminating optics which are exposed when the outlet channel is removed can be checked for dirt and, if necessary, cleaned.

In this connection, it is also possible to form the outlet channel from a plurality of parts, each of which can be separated from the handpiece with little effort so that they can be cleaned and disinfected easily. For example, this could be the inner and outer bushing of an outlet channel constructed as a double-walled tube which are fastened to the base body of the handpiece by catches or screws.

Further, it can be advantageous that at least one opening is provided in the wall of the outlet channel in the region between the terminating optics and the through-openings, wherein the inner region of the outlet channel communicates with the open air through this opening. In this way, not only is the air flow which is sucked out and carried off laterally through the through-openings in the wall of the outlet channel guided in the direction of the outlet opening through the through-openings to the exhaust device, but a flow direction is also generated proceeding from the terminating optics in the direction of the through-openings, so that a more reliable air suction and cleaning of the inner region of the outlet channel is ensured in the portion located between the through-openings and the terminating optics.

A further very advantageous construction consists in that the portion of the outlet channel in which the through-openings are provided is arranged so as to be rotatable about the center axis of the laser beam relative to the portion of the outlet channel in which no through-openings are provided. In this way, especially when the through-openings are not arranged in a radially symmetric manner around the center axis of the laser beam, the portion of the outlet channel having the through-openings can be adjusted in such a way, depending on the orientation of the handpiece, by rotation about the center axis of the laser beam that air extraction is carried out with optimum efficiency.

Further, it can be advantageous when only one through-opening is provided in the wall of the outlet channel and when this through-opening is formed, for example, as a slot which extends concentrically about the center axis of the laser beam. This ensures that the extraction of the air flow and the removal laterally through the wall of the outlet channel are carried out in a uniform manner around the entire circumference of the wall of the outlet channel.

Further, flow directing devices can be provided in the inner region of the outlet channel in front of at least one of the through-openings. These flow directing devices can be constructed as thin-walled tongues which project from the wall of the inner region into the outlet channel and are arranged in such a way that their distance from the wall increases with decreasing distance from the outlet opening; that is, they project in the direction opposite to the flow direction into the inner region and accordingly promote the lateral deflection of the air flow in the direction of the through-openings. It is also possible to provide a thin-walled, circular funnel as a flow directing device which projects conically into the inner region of the outlet channel proceeding from the wall and whose diameter becomes narrower in the direction of the outlet opening. In this way, the air flow is deflected through the conical funnel wall laterally in the direction of the through-openings resulting in improved flow conditions in the outlet channel.

In a further construction, a spacer can be provided in the vicinity of the outlet opening between the outlet opening and the treated area. The spacer can be constructed, for example, as a rod-shaped part whose length, measured in the direction of the laser beam, corresponds to the distance to be maintained between the outlet opening and the skin portion during the operation of the arrangement. Alternatively, the spacer can be constructed as a transparent sleeve made, for example, from transparent plastic material which can be fitted to the outlet end and whose length likewise corresponds to the distance between the outlet opening and the skin portion. In this way, it is possible for the treating physician to maintain the distance between the outlet opening and the skin portion with sufficient accuracy.

In connection with the constructions mentioned above, another possible variant, for example, consists in that the spacer constructed as a sleeve is held so as to be displaceable in the direction of the surface to be treated, so that it is possible during treatment to readjust, as necessary, the desired distance between the outlet opening and the skin portion to be treated. For this purpose, complementing catch elements can be provided at the spacer and outlet channel, so that the spacer can be locked and accordingly fixed in different displacement positions. It is also possible to construct the transparent sleeve as an optical filter. For this purpose, the material provided for the sleeves is transparent for the visible wavelength spectrum, but opaque for the wavelength of the utilized laser radiation. In this way it is possible for the treating physician to observe the relevant skin portion during the treatment without exposing himself to dangerous reflected laser radiation.

Finally, the exhaust device can be advantageously outfitted with an air filter unit.

The invention will be described more fully hereinafter with reference to an embodiment example.

DESCRIPTION OF THE PREFERRED EMBODIMENTS

Figure 1:
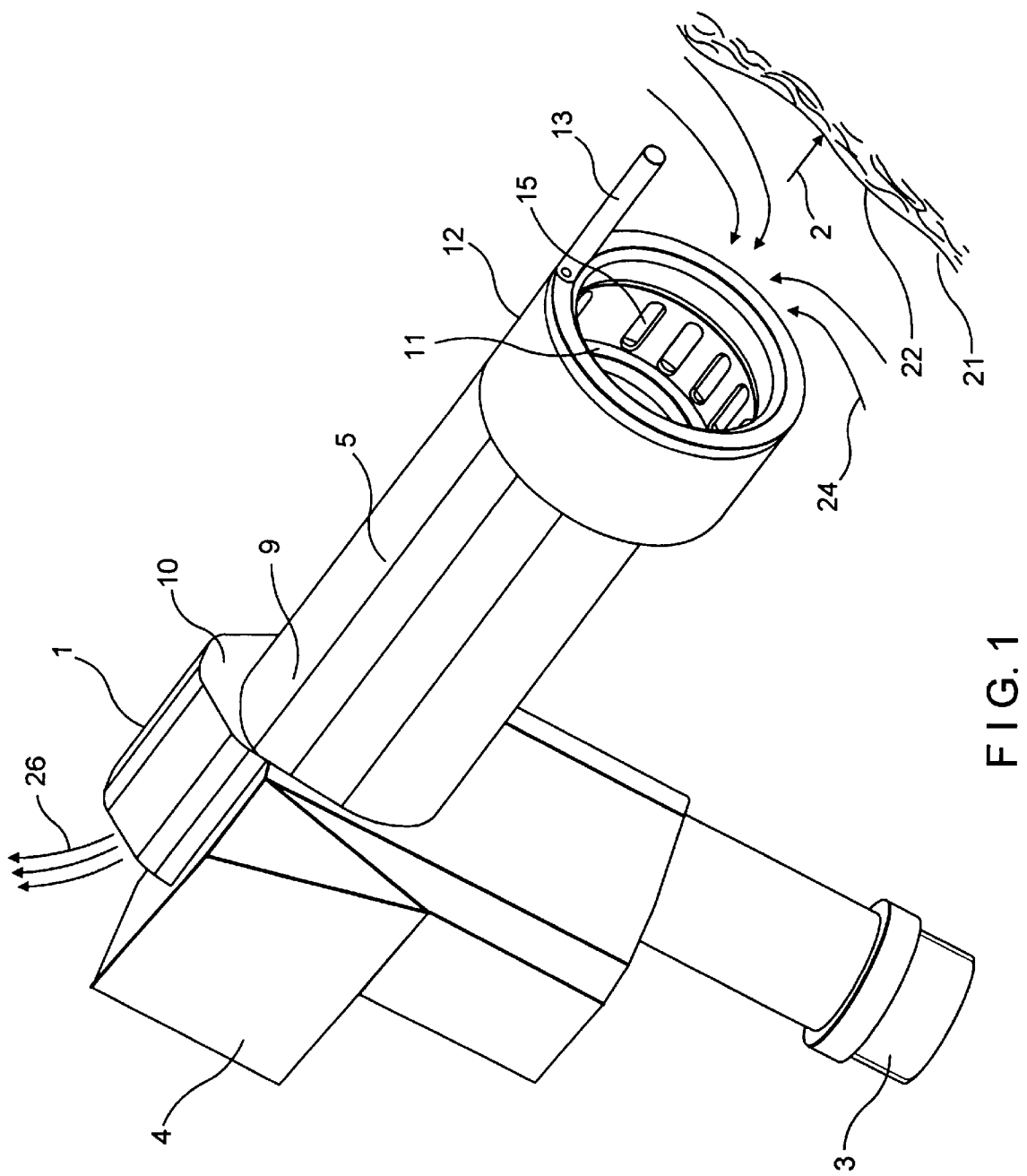
FIG. 1 a general drawing of a handpiece according to the invention.

The handpiece 1 shown in FIG. 1 serves to direct a laser beam 2 onto a portion of skin 21, for example, for the treatment of exophytic lesions or for skin resurfacing. The handpiece 1 has a coupling 3 for connecting to a beam guiding unit for guiding the laser beam 2 from a radiation source to the handpiece 1. The radiation source is not shown in the drawing, but may be, for example, a commercially available Er:YAG type pulsed laser with a radiation wavelength of 2.94 μm and a pulsing force of approximately 100 mJ with a pulse duration of 350 μs. The beam guiding unit, which is also not shown in the drawing, can be constructed, for example, as a fiber-optic device, e.g., a light-waveguide, or from a plurality of rigid members in an articulated connection with one another. In the latter case, the laser beam 2 is transmitted, from one member to the other via mirrors which are provided in the articulations, from the radiation source to the handpiece. Beam guiding units of this kind are known in the prior art. They permit spatial separation of the laser radiation source and handpiece 1, so that the handpiece can have a compact, light construction which consequently enables easy handling when manually directing onto the skin portion to be treated.

Further, a laser scanning device 4 is provided at the handpiece 1. This laser scanning device 4 causes a deflection of the laser radiation 2 by an angle α over the treated area 22 on the skin portion 21. The use of the laser scanning device 4 in a handle 1 of the type described above has the advantage that the relatively large treatment area 22 which corresponds to the deflecting range of the laser radiation 2 over the angular range α onto the skin portion 21 can be medically treated without having to change the manual orientation of the handpiece 1 on the skin portion 21.

Alternatively, the handpiece 1 can also be constructed without a laser scanning device 4 or without the scanning function, i.e., can be operated with a laser beam that is not deflected. In this case, if the orientation of the handpiece 1 were to remain unchanged, the laser radiation 2 would always only be directed onto the skin portion 21 corresponding to the diameter of the laser beam 2, i.e., the treated area 22 would then only be as large as the diameter of the laser beam. Both modes of operation are common, and handpieces 1 which permit only one or the other of these two operating modes are known. For special applications of photoablation in treatment of skin, these operating modes offer various advantageous and are selected depending on these applications.

The handpiece 1 is further outfitted with a handle 5 which is grasped in the hand of the treating physician during the ablation procedure, who directs the handpiece 1 and accordingly the laser beam 2 onto the portion of skin to be treated by changing direction. The handle 5, in turn, encloses a tubular outlet channel 6 (see FIG. 2) for the laser beam 2. This outlet channel 6 which can be produced from an aluminum alloy or from titanium, has, for example, a circular cross section which extends from its end portion 9 facing the scanning device 4 to its end portion 12 remote of the scanning device 4 and thus forms a cylindrical inner region 7 surrounding the laser beam 2, wherein the center axis 8 of the laser beam is located approximately in the center of the inner region 7. The center axis 8 of the laser beam is identical to the position occupied by the laser beam 2 when deflection is not carried out; the maximum deflecting positions may be those positions occupied by the laser beam at a deflection of α/2 toward both sides of the center axis 8 of the laser beam.

Terminating optics (not shown) for the laser beam 2 are located at the end portion 9 of the inner region 7 in the outlet channel 6, i.e., at the point where the outlet channel 6 adjoins the laser scanning device 4. The laser beam 2 extends from the radiation source, through the beam guiding unit to the laser scanning device 4 in the handpiece 1 and is thus surrounded up to this point by optical and mechanical components and is guided within these components in a protected manner. However, the laser beam 2 exits these components at the terminating optics for the laser beam 2 which is arranged at the end portion 9 in the inner region 7 of the outlet channel 6, and, at this point, passes into the open air. Although the laser beam 2 now passes into the open air, it is still enclosed by the outlet channel 6 on its way to the skin portion 21 to be treated. It extends within the outlet channel 6, starting at the terminating optics, until the end portion 12 of the outlet channel 6 through the inner region 7, then exits through the outlet opening 11 at this point and continues on to the skin portion 21 without protection or shielding.

A spacer 13 is arranged in the front region of the outlet opening 11. The spacer 13 is constructed in a rod-shaped manner and corresponds in length to the distance to be maintained between the outlet opening 11 and the skin portion 21 during the dermatological treatment. It is necessary to maintain this distance so as to ensure a defined influence on the skin surface or on deeper-lying layers of the skin depending on the intensity of the laser beam 2. When the distance is too small, the intensity of the laser radiation 2 in the vicinity of the skin is too great and causes an unintentionally harsh effect on the skin. If the distance is too great, the influence is insufficient because of the reduced intensity of the laser radiation 2. The spacer 13 is accordingly supported on the surface of the skin during treatment in a light and sensitive manner and thus serves to position the handpiece 1 over the skin portion 21 to be treated. The spacer 13 is constructed, for example, as a round metal rod with a diameter of 4 mm and a length of 30 mm. It can also be constructed as a transparent sleeve with lateral recesses bordering on the skin portion, as was already mentioned.

Depending on the radiation intensity or the purpose of treatment, e.g., for treating the surface of the skin or deeper-lying layers, spacers 13 of different lengths can be used. For the purpose of easy exchangeability, the spacer 13 is connected with the front region of the outlet opening 11 by means of a simple plug-in socket having a sliding fit.

In order to allow the particles removed from the surface of the skin during treatment with the laser beam 2, as well as the resulting fumes, to be carried off in such a way that they cannot settle on the terminating optics and such that there is no odor or other annoyance for the medical personnel and patient, the entire area (22) is subjected to a suction vacuum during the treatment in accordance with the method according to the invention.

For this purpose, the outlet opening 11 of the handpiece 1 is connected, according to the invention, with an air exhaust device and thus takes over the function of the mouth opening of the suction tube. As is shown in FIG. 1, the wall 14 of the outlet channel 6 surrounds the laser beam 2 during operation of the arrangement and is provided, proceeding from the inner region 7, with a plurality of through-openings 15. These through-openings 15 connect the inner region 7 of the outlet channel 6 with the outside 16 of the outlet channel 6. Proceeding from the outside 16, the through-openings 15 are connected with a suction device. For this purpose, a cavity 17 is arranged at the outside 16 of the outlet channel 6, the enclosure 23 of this cavity 17 being connected with the outside 16 so as to be hermetically sealed, wherein it is ensured that the sucked in air can pass freely from the outlet opening 11 into the inner region of the outlet channel 6 and through the through-openings 15 into the cavity 17.

The cavity 17 is connected with an exhaust device in the direction opposite to that in which the enclosure 23 of the cavity 17 is joined to the outside 16 of the outlet channel 6. The exhaust device serves to generate an air flow 24 which comes from the skin portion 21 to be treated and is directed through the outlet opening 11 into the inner region 7 of the outlet channel 6 and then through the through-openings 15 and the cavity 17 to the exhaust device. The exhaust device is not shown in the drawing. The "SUSY" gas exhaust system manufactured by Drägerwerk Aktiengesellschaft, Lübeck, Germany, can be used as an exhaust device. The extracted air flow can be regulated with this system up to a maximum volume flow of 650 liters per minute. The exhaust system has an air filter device and noise protection device. It can be coupled to the cavity 17 by means of accessories (hose set, adapter set) supplied with the device. For this purpose, the enclosure 23 of the cavity 17 need only be adapted to the adapter mouthpiece at a freely selectable location such that the adapter mouthpiece can be attached.

Figure 2:
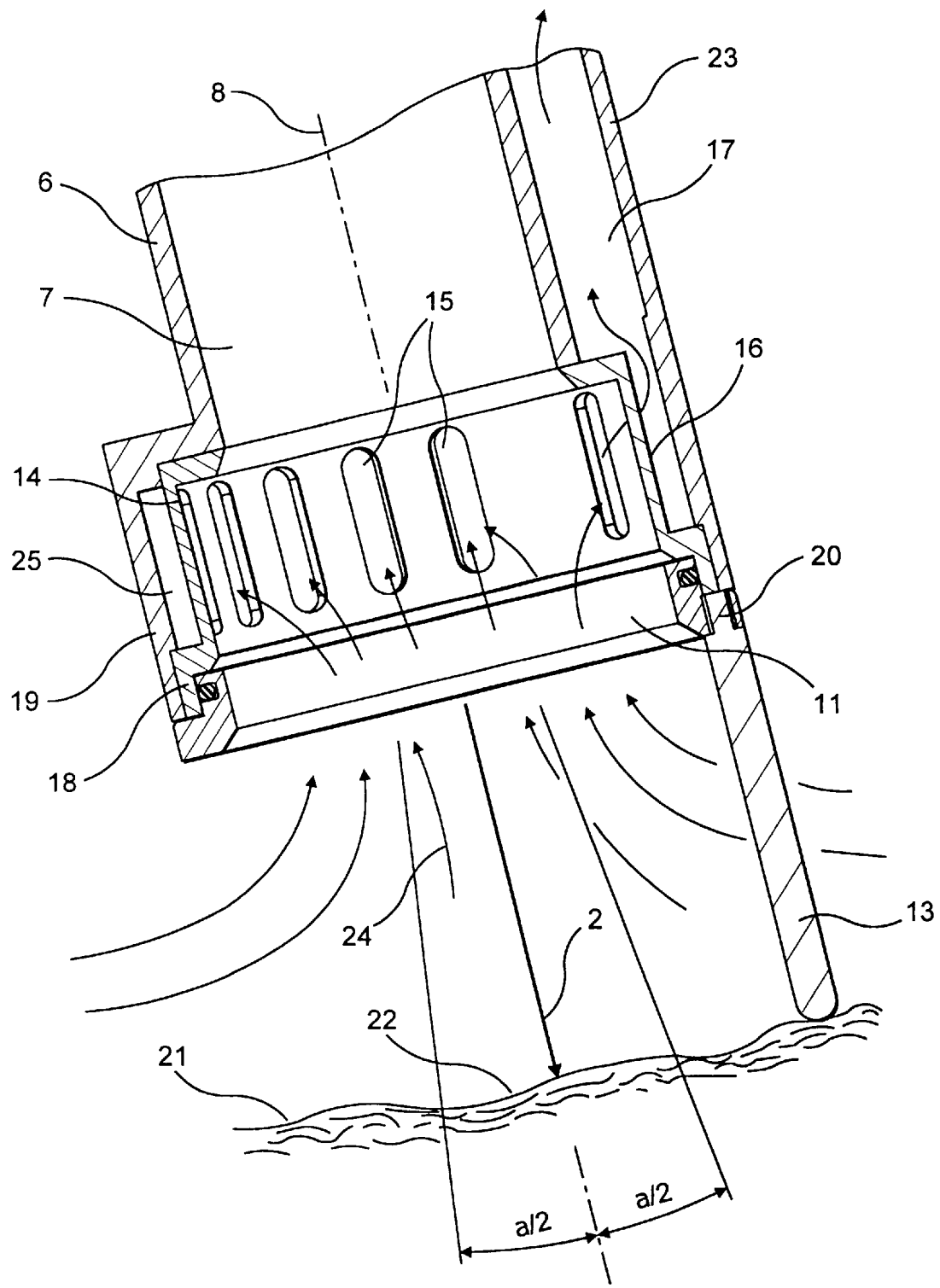
FIG. 2 a section of the handpiece according to the invention from FIG. 1.

The through-openings 15 are constructed, for example, as slots, as can be seen from FIG. 2, and are arranged at different distances from one another around the center axis 8 of the laser beam. The longitudinal edges or side edges of the slots are oriented parallel to the center axis 8 of the laser beam. The distances between the slots in the circumferential direction are smallest at a first position on the circumference of the wall 14 and greatest at a second position located diametrically opposite from the first position at the circumference of the wall 14. The slots are dimensioned in such a way that the sum of their opening surface areas through the wall 14 roughly corresponds to the cross-sectional area of the outlet opening 11, which results in advantageous flow conditions.

As is further shown in FIG. 2, the longitudinal portion of the outlet channel 6 in which the through-openings 15 are located is arranged so as to be rotatable about the center axis 8 of the laser beam relative to the rest of the longitudinal portion of the outlet channel 6 directed toward the end portion 9 in which no through-openings 15 are provided. For this purpose, the portion with the through-openings 15 is constructed as a bushing 18 which is held in a widened portion 19 of the tubular outlet channel 6. The widened portion 19 is provided near the end portion 12 of the outlet channel 6 as can be seen in FIG. 2.

During the treatment of a skin portion 21 by means of the handpiece according to the invention, particles and fumes are released from the target area 22. When the exhaust device is put into operation in addition to the laser treatment device, air is sucked in circumferentially from the region between the target area 22 on the skin portion 21 and the outlet opening 11 due to the suction effect when the volume flow is suitably adjusted. That is, the air flows from all sides against the skin portion 21, is sucked into the outlet opening 11, flows into the inner region 7 of the outlet channel 6 as is shown by the air flow 24, and then flows through the through-openings 15 into the cavity 17 and, from there, into the exhaust device where the particle and fumes are captured in the air filter device. Accordingly, personnel and patients are protected from breathing in the particles and foul-smelling fumes. Further, the particles and fumes are prevented from advancing past the outlet channel 6 to the terminating optics at the end portion 9 of the outlet channel 6 where they could settle on the terminating optics. Before the particles and the unpleasant fumes can reach the terminating optics, they are removed from the outlet channel 6 laterally through the wall 14.

A further problem is solved by the arrangement according to the invention: When the laser operates on the treatment area in a rapid sequence of pulses by means of the scanner, there is a risk that the released particles and gas fumes will stay in the beam path of the laser light and cross the beam path resulting in irregular energy distribution. This irregular energy distribution in the laser beam can, in turn, have a negative influence on the results of treatment and therapy. However, by means of the arrangement according to the invention, these particles and fumes are quickly removed from the radiation area so that these disadvantageous consequences cannot even arise. A partial absorption of the laser radiation due to air contamination of this kind is accordingly ruled out to a very great extent. The effectiveness of the utilized handpiece is increased in this way.

While the foregoing description and drawings represent the preferred embodiments of the present invention, it will be obvious to those skilled in the art that various changes and modifications may be made therein without departing from the true spirit and scope of the present invention.

What is claimed is:

1. In a method for photoablation in the field of dermatological medicine in which an area on a skin surface is swept over by a laser beam which passes the open air and thus subjected to treatment, an improvement comprising the step of subjecting the area to be treated to a suction vacuum during treatment over its entire extent.

2. The method for photoablation according to claim 1, wherein the suction vacuum is applied by means of a suction tube positioned over the target area.

3. The method for photoablation according to claim 2, wherein the cross section of the suction tube arranged over the treatment area essentially corresponds to the surface area of the treatment area.

4. The method for photoablation according to claim 3, wherein the cross section of the suction tube arranged over the treatment area is slightly larger than the treatment area.

5. The method for photoablation according to claim 4, wherein the cross section of the suction tube arranged over the treatment area is 5% to 10% greater than the treatment area.

6. The method for photoablation according to claim 1, wherein the edge of the mouth opening of the suction tube is positioned at a distance from the treated area of 10 mm to 80 mm.

7. The method for photoablation according to claim 1, wherein the suction vacuum is selected in such a way that the maximum flow velocity in the mouth opening of the suction tube is 650 liters per minute.

8. The method for photoablation according to claim 7, wherein the suction vacuum is selected in such a way that the mean flow velocity in the mouth opening of the suction tube is 400 liters per minute.

9. In an arrangement for photoablation in the field of dermatological medicine by means of laser radiation with optical component groups for protected guidance of the laser radiation, with terminating optics at the point where the laser radiation passes into the open air, and with a tubular outlet channel by which the free laser radiation is surrounded proceeding from the terminating optics and which has an outlet opening for the laser radiation at its end portion opposite from the terminating optics, wherein, during treatment, the laser radiation and the outlet channel are directed toward an area to be treated on the surface of the skin and the outlet opening is positioned near the area, an improvement comprising that the outlet opening communicates with a device for generating a suction vacuum.

10. The arrangement according to claim 9, wherein an exhaust device is provided as a device for generating a suction vacuum, in that the wall of the tubular outlet channel has at least one through-opening extending from its inner region to its outer side, and in that the outer side is connected to the exhaust device.

11. The arrangement according to claim 9, wherein a plurality of through-openings are provided in the wall of the outlet channel, wherein these through-openings are distributed in a radially symmetric manner along a circumference extending around the center axis of the laser beam.

12. The arrangement according to claim 11, wherein a plurality of through-openings are provided in the wall of the outlet channel, wherein the through-openings are arranged so as to be distributed along the circumference extending around the center axis of the laser beam at different distances from one another.

13. The arrangement according to claim 11, wherein the circumference on which the through-openings are arranged around the center axis of the laser beam is provided near the outlet opening of the outlet channel.

14. The arrangement according to claim 11, wherein all of the through-openings in the wall of the outlet channel have the same geometric shape.

15. The arrangement according to claim 14, wherein all of the through-openings are shaped as circular holes.

16. The arrangement according to claim 14, wherein all through-openings are formed as slots, wherein the longer side edge of each slot is oriented parallel to the center axis of the laser beam.

17. The arrangement according to claim 14, wherein all through-openings are formed as trapezoidal slots, wherein the smaller slot width is oriented toward the outlet opening.

18. The arrangement according to claim 10, wherein all through-openings have the same distance from the outlet opening considered in the longitudinal direction of the terminating optics.

19. The arrangement according to claim 10, wherein the through-openings are arranged on a plurality of circumferences extending around the center axis of the laser beam, wherein the circumferences are provided at different distances from the outlet opening measured in the longitudinal direction of the terminating optics.

20. The arrangement according to claim 9, wherein the outlet channel is constructed as a double tube, wherein the core region of the double tube is identical to the inner region of the outlet channel, the inner surface of the double tube is identical to the wall of the outlet channel, the through-openings lead from the core region into the intermediate region between the inner surface of the double tube and the outer surface of the double tube, and the intermediate region is connected with the exhaust device.

21. The arrangement according to claim 20, wherein the outer surface of the double tube is constructed as a handle.

22. The arrangement according to claim 9, wherein the outlet channel is connected with the rest of the component parts of the arrangement so as to be hermetically sealed by its end portion located at the terminating optics, to be detachable.

23. The arrangement according to claim 9, wherein at least one opening is provided in the wall of the outlet channel in the region between the terminating optics and the through-openings, wherein the inner region of the outlet channel communicates with the open air through this opening.

24. The arrangement according to claim 9, wherein the portion of the outlet channel in which the through-openings are provided is arranged so as to be rotatable about the center axis of the laser beam relative to the portion of the outlet channel in which no through-openings are provided.

25. The arrangement according to claim 9, wherein only one through-opening is provided in the wall of the outlet channel.

26. The arrangement according to claim 25, wherein this one through-opening is formed as a slot which extends concentrically about the center axis of the laser beam.

27. The arrangement according to claim 9, wherein a flow directing device is provided in the inner region of the outlet channel in front of at least one of the through-openings.

28. The arrangement according to claim 27, wherein there are provided flow directing devices which are constructed as thin-walled tongues which project from the wall into the inner region of the outlet channel, wherein the distance of the tongues from the wall increases with decreasing distance from the outlet opening.

29. The arrangement according to claim 27, wherein the flow directing device is constructed as a thin-walled funnel which projects into the inner region of the outlet channel proceeding from the wall, wherein its diameter becomes narrower in the direction of the outlet opening.

30. The arrangement according to claim 9, wherein a spacer is provided between the outlet opening and the treated area.

31. The arrangement according to claim 30, wherein the spacer is constructed as a rod-shaped part whose length, measured in the direction of the laser beam, corresponds to the distance to be maintained between the outlet opening and the skin portion during the dermatological treatment.

32. The arrangement according to claim 30, wherein the spacer is constructed as a transparent sleeve whose length, measured in the direction of the laser beam, corresponds to the distance to be maintained between the outlet opening and the skin portion during the dermatological treatment.

33. The arrangement according to claim 30, wherein there is provided a plurality of spacers of different lengths which are individually interchangeable, wherein complementing catch elements are arranged at the outlet opening on the one hand and at the spacers on the other hand as fastening means.

34. The arrangement according to claim 9, wherein the exhaust device is outfitted with an air filter unit.

35. The method for photoablation according to claim 1, wherein the edge of the mouth opening of the suction tube is positioned at a distance from the treated area of 15 mm to 60 mm.

36. The method for photoablation according to claim 1, wherein the edge of the mouth opening of the suction tube is positioned at a distance from the treated area of 20 mm to 50 mm.

37. The method for photoablation according to claim 1, wherein the edge of the mouth opening of the suction tube is positioned at a distance from the treated area of 30 m to 35 mm.

* * * * *